Sept. 20, 1955 F. W. ANDERSON Plant Pat. 1,420

NECTARINE TREE

Filed Jan. 10, 1955

WITNESS

Addison F. Avery

INVENTOR

Frederic W. Anderson

Webster & Webster

ATTYS.

United States Patent Office

Plant Pat. 1,420

Patented Sept. 20, 1955

1,420

NECTARINE TREE

Frederic W. Anderson, Merced, Calif.

Application January 10, 1955, Serial No. 481,050

1 Claim. (Cl. 47—62)

This invention relates to a new and distinct variety of nectarine tree developed by me in the course of an extensive program seeking new varieties of nectarines which bear fruit having characteristics which are highly commercially desirable; the fruit of the present variety being distinctive—especially in relation to the John Rivers nectarine (unpatented), and the Sungrand nectarine (United States Plant Patent No. 974)—in the following respects:

As compared with such John Rivers nectarine which is presently the leading nectarine in orchard acreage in California, the instant variety ripens at approximately the same time, but the fruit is fifty percent larger in size; much firmer and remains so longer; has yellow instead of white flesh; and the skin is yellow, almost completely overspread with bright red at the firm ripe stage for long distance shipping.

As compared with the Sungrand nectarine, the present variety is generally similar in tree and fruit characteristics, but the fruit ripens approximately two weeks earlier.

This new and distinct variety of nectarine tree was originated by me in my experimental nursery at Le Grand, Merced County, California, as an open-pollinated seedling of such Sungrand nectarine. When I recognized the novel and commercially desirable characteristics of the fruit, the variety was selected for subsequent propagation; asexual reproduction having been accomplished by top working—specifically by budding—on mature orchard trees. Such asexual reproductions, when they came into bearing, were found to retain all of the characteristics of the original tree and the fruit thereof.

The asexual reproduction of the variety, as above, was accomplished by me in my experimental nursery located as aforesaid.

Figure 1:
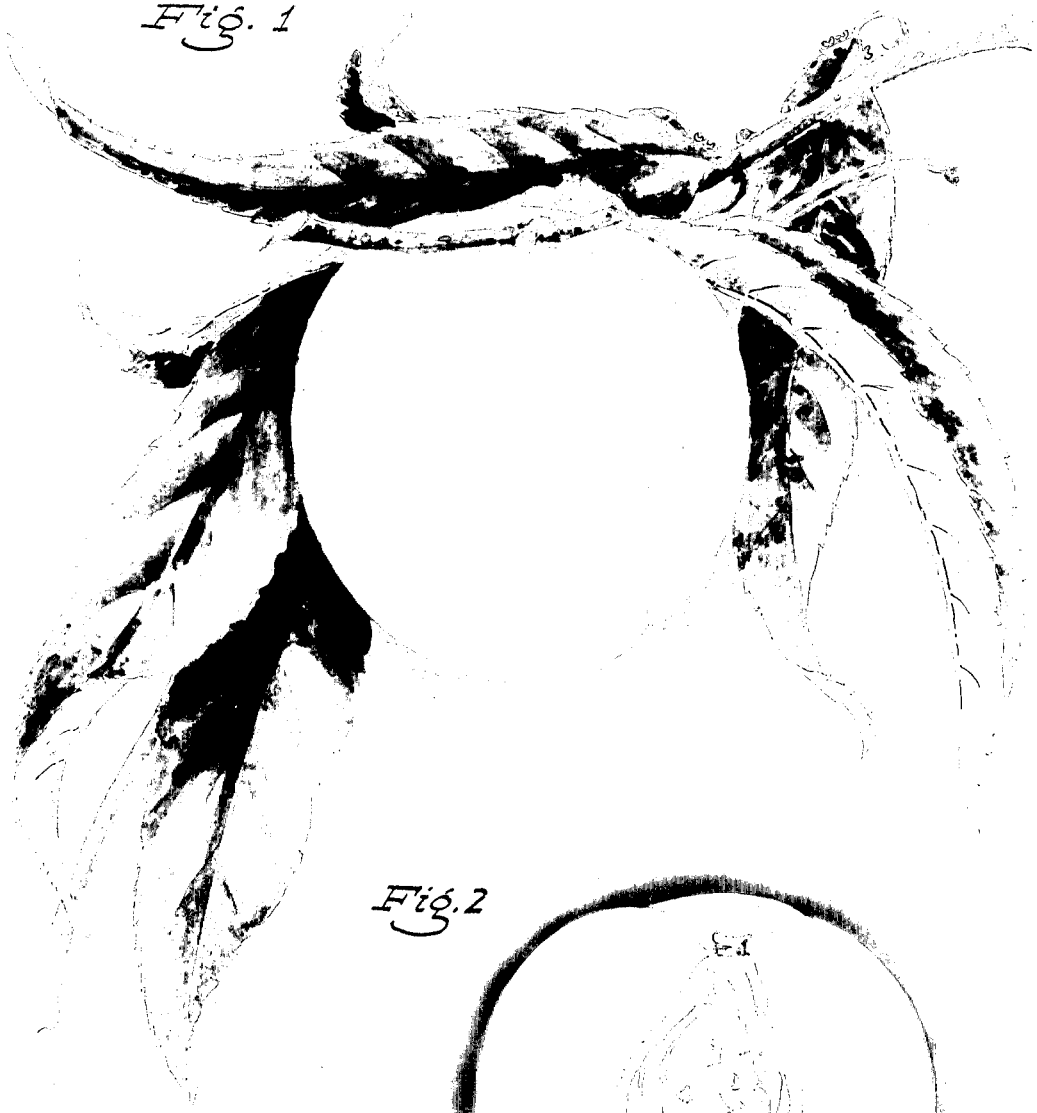
Fig. 1 is a perspective view of the fruit, together with a twig and leaves of the present variety.
Figure 2:
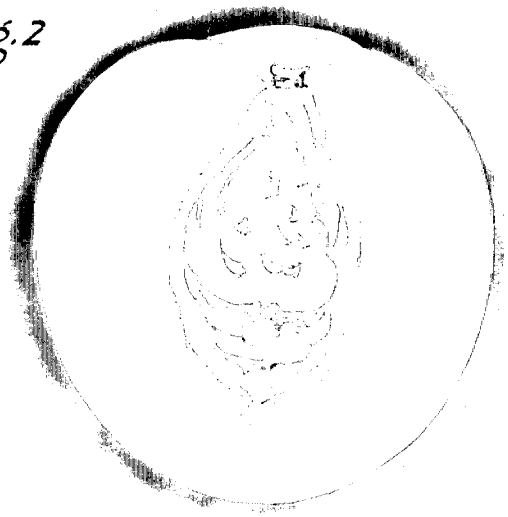
Fig. 2 is a sectional elevation of the fruit with the stone exposed.
Figure 3:
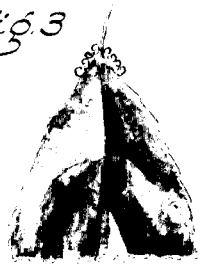
Fig. 3 is a fragmentary sectional elevation of one of the leaves showing particularly the glands.

Referring now more specifically to the pomological details of this new and distinct variety of nectarine tree, the following is an outline description thereof; all major color plate identifications being by reference to Maerz and Paul Dictionary of Color:

Tree:
- *Size.*—Large.
- *Vigor.*—Vigorous.
- *Growth.*—Upright.
- *Shape.*—Vase formed.
- *Production.*—Very productive.
- *Bearing.*—Regular bearer.

Trunk:
- *Size.*—Medium.
- *Surface.*—Medium.

Branches:
- *Size.*—Medium.
- *Surface.*—Medium.
- *Lenticels.*—Number—medium.

Leaves:
- *Size.*—Large. Average length — 6½"; average width 1½".
- *Thickness.*—Medium.
- *Margin.*—Crenate.
- *Petiole.* — Length — medium. Thickness — medium.
- *Glands.* — Average number — four. Size — medium. Form—reniform. Position—usually two on petiole and two or more on blade.
- *Stipules.*—None.
- *Color.*—Top side—medium green (22–L–6). Under side—lighter green (21–K–6).

Flower Buds:
- *Size.*—Medium.
- *Length.*—Medium.

Flowers:
- *Date of bloom.*—Usually about with the Burbank Elberta peach (United States Plant Patent No. 15).
- *Size.*—Large.

Fruit:
- *Date of first picking.*—June 18, 1954.
- *Date of last picking.*—June 28, 1954.
- *Maturity when described.*—Eating ripe.
- *Size.*—Uniform; large. Average diameter axially—2¾". Average transversely in suture plane—2 11/16".
- *Form.*—Oblong; compressed laterally toward suture.
- *Suture.*—Deep; extends over entire circumference.
- *Ventral surface.*—Rounded slightly.
- *Cavity.*—Elongated in suture plane, with suture showing on both sides. Average depth—½". Average breadth—9/16". Markings—red.
- *Base.*—Rounded.
- *Apex.*—Short.
- *Pistil point.*—Apical; very short.

Skin:
- *Texture.*—Thick; tough.
- *Tendency to crack.*—None.
- *Down.*—Wanting.
- *Color—when firm ripe.*—Yellow (10–L–6), almost completely overspread with red (4–L–9), shading to darker red (7–L–6).

Flesh:
- *Juice.*—Moderate; rich.
- *Texture.*—Firm; meaty.
- *Fibers.*—Few.
- *Ripens.*—Even.
- *Flavor.*—Subacid.
- *Aroma.*—Distinct.
- *Eating quality*—Fair to good.
- *Color.*—Yellow (9–J–4 shading to 9–I–7), mottled with red (3–K–10) next to the skin and more pronounced near the apex.
- *Surface of pit cavity.*—Yellow—as flesh—but with a slight greenish cast, with yellow fibers.

Stone:
- *Type.*—Semi-free.
- *Size.* — Large. Average length — 1¾". Average breadth—1". Average thickness—⅞".
- *Form.*—Obovoid.
- *Hilum.*—Oblong.
- *Surface.*—Regularly furrowed throughout. Pitted from base to above center.
- *Ridges.*—Ridged throughout. Rounded. On either side continuous.
- *Pits.*—Angular.
- *Ventral edge.*—Thick, without wing throughout.
- *Dorsal edge.*—Full, with shallow groove throughout.
- *Color.*—Light brown (11–I–8).

Use: Market; local; dessert; long distance shipping.
Keeping quality: Good
Shipping quality: Good.

The tree and its fruit herein described may vary in slight detail due to climatic and soil conditions under which the variety may be grown.

The following is claimed:

A new and distinct variety of nectarine tree, substantially as described and illustrated, characterized by a general resemblance to the parent Sungrand nectarine but bearing fruit which ripens approximately two weeks earlier, and about with the John Rivers nectarine; and further characterized by fruit which is semi-freestone, large, firm yellow-fleshed with red mottling next to the skin, and skin which is yellow almost completely overspread with red when the fruit is firm ripe.

No references cited.